United States Patent [19]

Brady et al.

[11] Patent Number: 5,582,613
[45] Date of Patent: Dec. 10, 1996

[54] APPARATUS AND METHODS FOR CONTROLLED INSERTION OF INTRAOCULAR LENSES

[75] Inventors: Daniel G. Brady, Mission Viejo; Thomas M. McNicholas, Laguna Niguel, both of Calif.

[73] Assignee: Allergan, Waco, Tex.

[21] Appl. No.: 323,172

[22] Filed: Oct. 14, 1994

Related U.S. Application Data

[63] Continuation-in-part of Ser. No. 154,240, Nov. 18, 1993, abandoned, and a continuation-in-part of Ser. No. 235,444, Apr. 29, 1994.

[51] Int. Cl.$^6$ ....................................................... A61F 9/00
[52] U.S. Cl. ............................................................. 606/107
[58] Field of Search ................................ 606/107; 623/4, 623/6; 128/898

[56]     References Cited

U.S. PATENT DOCUMENTS

| | | |
|---|---|---|
| 450,266 | 4/1891 | Truax . |
| 2,450,138 | 9/1948 | Harwood . |
| 3,678,927 | 7/1972 | Soichet . |
| 3,703,174 | 11/1972 | Smith . |
| 4,026,281 | 5/1977 | Mayberry et al. . |
| 4,122,556 | 10/1978 | Poler . |
| 4,190,049 | 2/1980 | Hager et al. . |
| 4,198,980 | 4/1980 | Clark . |
| 4,214,585 | 7/1980 | Bailey, Jr. . |
| 4,244,370 | 1/1981 | Furlow et al. . |
| 4,249,271 | 2/1981 | Poler . |
| 4,251,887 | 2/1981 | Anis . |
| 4,253,199 | 3/1981 | Banko . |
| 4,257,521 | 3/1981 | Poler . |
| 4,298,994 | 11/1981 | Clayman . |
| 4,303,268 | 12/1981 | Davidson . |
| 4,325,375 | 4/1982 | Nevyas . |
| 4,373,218 | 2/1983 | Schachar . |
| 4,423,809 | 1/1984 | Mazzocco . |
| 4,446,581 | 5/1984 | Blake . |
| 4,449,257 | 5/1984 | Koeniger . |
| 4,462,404 | 7/1984 | Schwarz et al. . |
| 4,463,457 | 8/1984 | Kelman . |
| 4,468,820 | 9/1984 | Uhler et al. . |
| 4,490,860 | 1/1985 | Rainin . |
| 4,527,294 | 7/1985 | Heslin . |
| 4,573,998 | 3/1986 | Mazzocco . |
| 4,600,004 | 7/1986 | Lopez et al. . |
| 4,619,657 | 10/1986 | Keates et al. . |
| 4,681,102 | 7/1987 | Bartell .................................... 606/107 |

(List continued on next page.)

FOREIGN PATENT DOCUMENTS

| | | |
|---|---|---|
| 0270257 | 8/1988 | European Pat. Off. . |
| 2191439 | 12/1987 | United Kingdom . |
| 8201646 | 5/1982 | WIPO . |
| 8808288 | 11/1988 | WIPO . |
| 9407436 | 4/1994 | WIPO . |
| 9420027 | 9/1994 | WIPO .................................... 606/107 |

OTHER PUBLICATIONS

Cataract Refract Surg., vol. 15, Mar. 1989, Christ et al.
Folding & Inserting Silicone Intraocular Lens Implants, Faulkner, Nov. 1987.
Microsert II™, Model IM002, Directions for Use with the Chiroflex™ II, Chiron IntraOptics, Jul. 1993.
IOL & Ocular Surgery News, vol. 1, No. 14 (Jul. 1983).
Staartrek–Staar Surgical Co. vol. 4, No. 1 pp. 1–7 Jul. 1988.

*Primary Examiner*—Glenn Dawson
*Attorney, Agent, or Firm*—Frank J. Uxa

[57]         ABSTRACT

Apparatus and methods for inserting foldable IOL's into the eye are disclosed. The present apparatus include a load chamber and an injection tube. A hand piece may be included which is structured to reinforce the injection tube, in particular the proximal end portion of the injection tube. The open distal end of the injection tube may be beveled, preferably so that the open distal end faces generally toward the right, so that the IOL can be inserted into the eye through a smaller incision in a controlled manner, for example, to reduce the need for post-surgical manipulation of the IOL in the eye. Methods for inserting IOL's into eyes of patients, particularly using the present apparatus, are also disclosed.

16 Claims, 2 Drawing Sheets

U.S. PATENT DOCUMENTS

| | | |
|---|---|---|
| 4,715,373 | 12/1987 | Mazzocco et al. . |
| 4,732,150 | 3/1988 | Keener, Jr. . |
| 4,747,404 | 5/1988 | Jampel et al. . |
| 4,759,359 | 7/1988 | Willis et al. . |
| 4,763,650 | 8/1988 | Hauser . |
| 4,765,329 | 8/1988 | Cumming et al. . |
| 4,769,034 | 9/1988 | Poley . |
| 4,781,719 | 11/1988 | Kelman . |
| 4,785,810 | 11/1988 | Baccala et al. . |
| 4,791,924 | 12/1988 | Kelman . |
| 4,813,957 | 3/1989 | McDonald . |
| 4,819,631 | 4/1989 | Poley . |
| 4,834,094 | 5/1989 | Patton et al. ............ 606/107 |
| 4,836,201 | 6/1989 | Patton et al. . |
| 4,844,065 | 7/1989 | Faulkner . |
| 4,844,093 | 7/1989 | Jampel et al. . |
| 4,880,000 | 11/1989 | Holmes et al. . |
| 4,917,680 | 4/1990 | Poley . |
| 4,919,130 | 4/1990 | Stoy et al. ................ 606/107 |
| 4,934,363 | 6/1990 | Smith et al. . |
| 4,976,716 | 12/1990 | Cumming . |
| 4,988,352 | 1/1991 | Poley . |
| 5,098,439 | 3/1992 | Hill et al. . |
| 5,123,905 | 6/1992 | Kelman ..................... 606/107 |
| 5,190,552 | 3/1993 | Kelman ..................... 606/107 |
| 5,260,021 | 11/1993 | Zeleznick . |
| 5,425,734 | 6/1995 | Blake ........................ 606/107 |
| 5,474,562 | 12/1995 | Orchowski et al. ....... 606/107 |
| 5,494,484 | 2/1996 | Feingold ................... 606/107 |

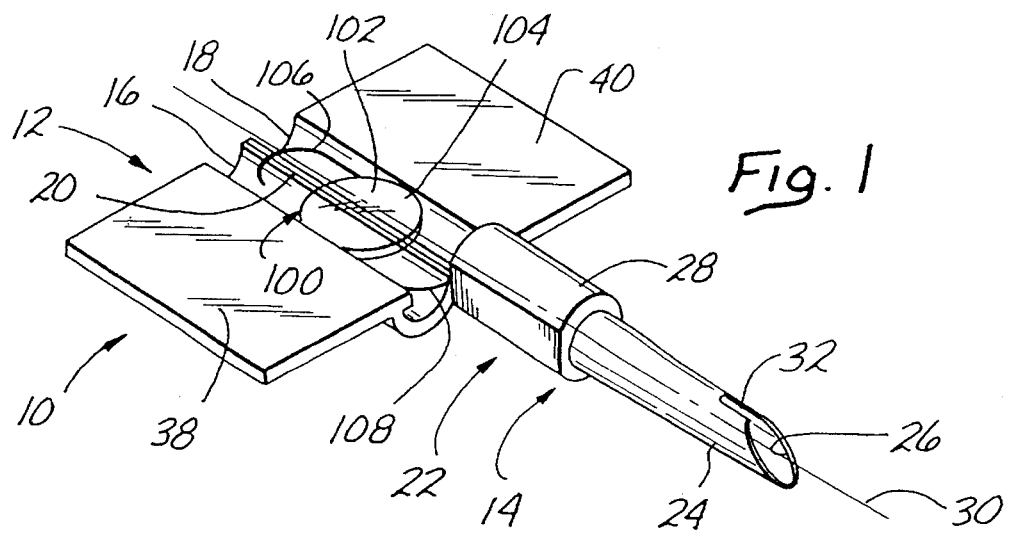
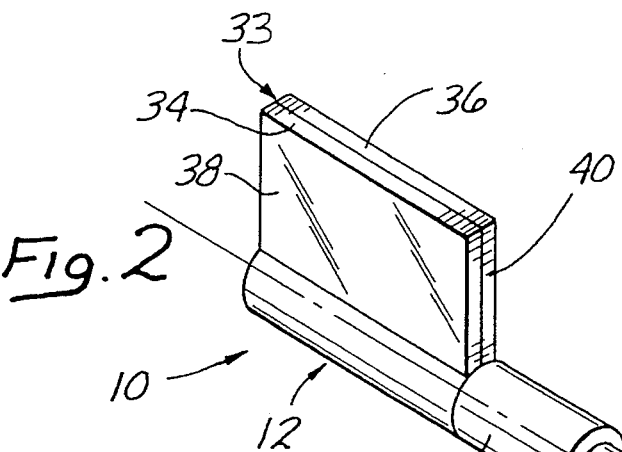
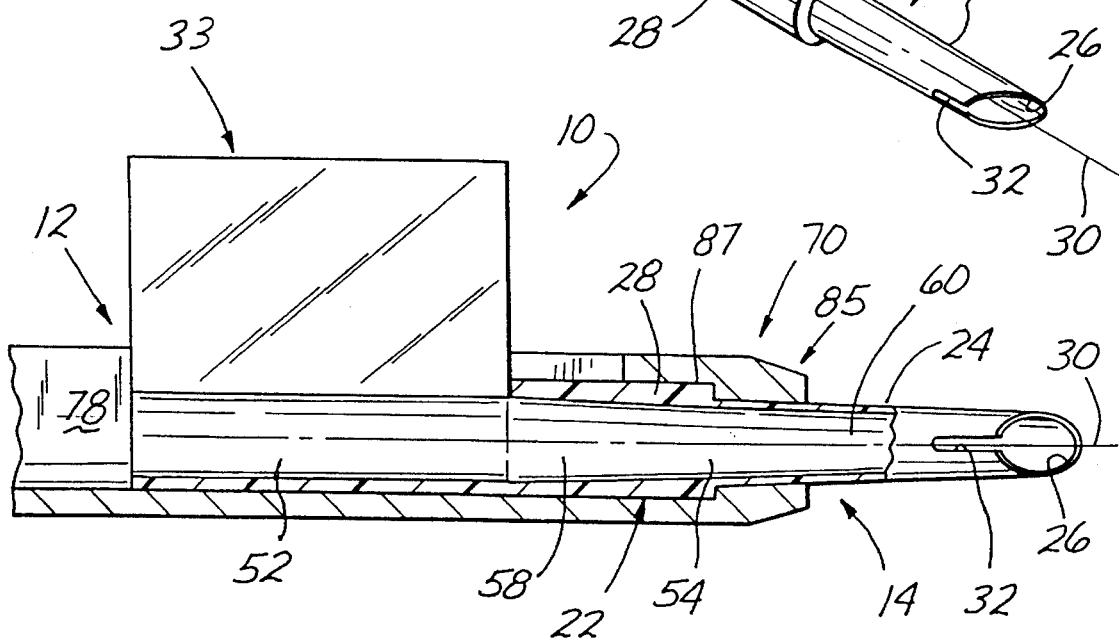

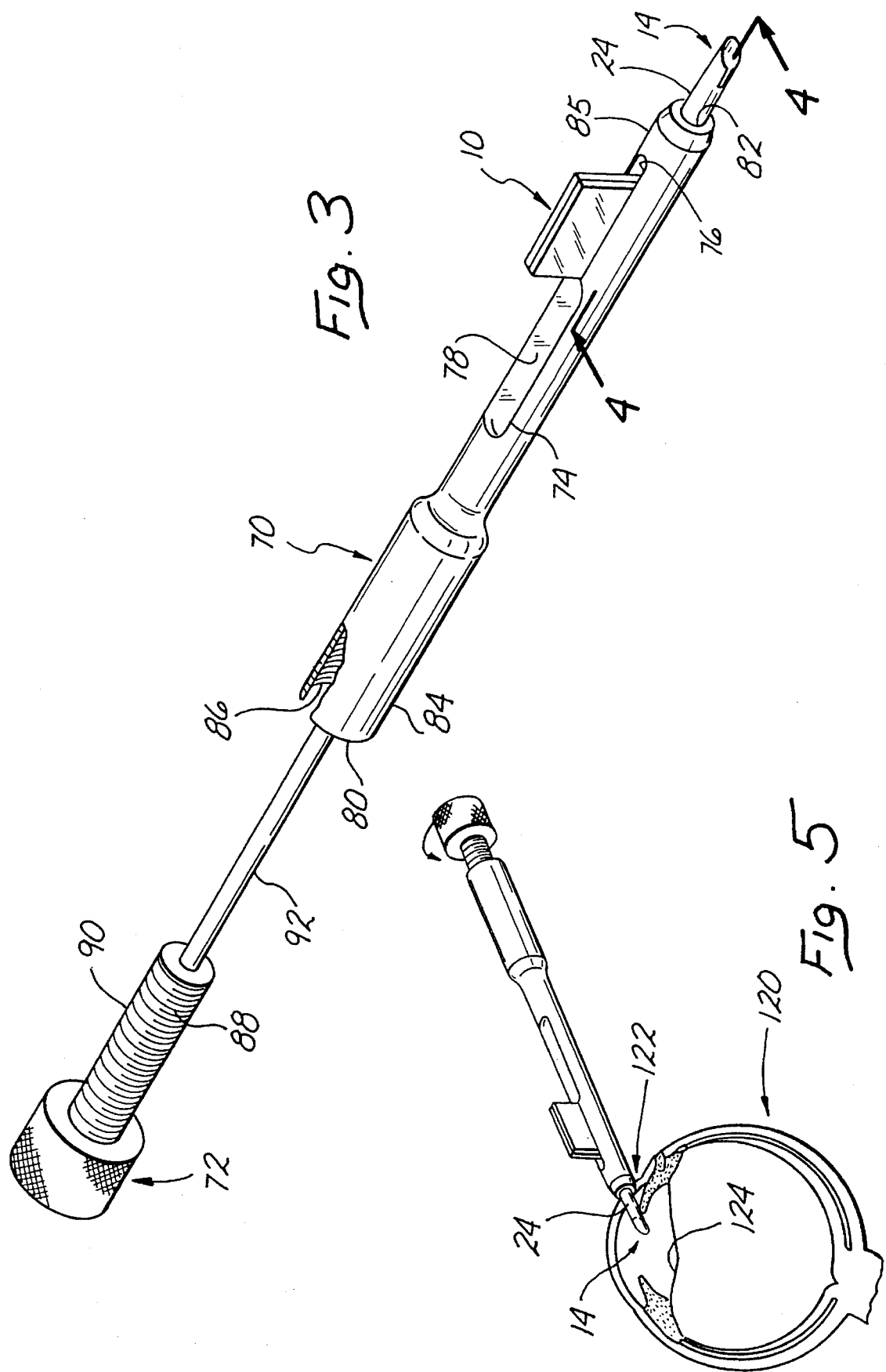

APPARATUS AND METHODS FOR CONTROLLED INSERTION OF INTRAOCULAR LENSES

RELATED APPLICATIONS

This application is a continuation-in-part of application Ser. No. 08/154,240 filed Nov. 18, 1993 now abandoned, and of Ser. No. 08/235,444 filed Apr. 29, 1994 now pending. The disclosure of each of these applications is incorporated in its entirety herein by reference.

FIELD OF THE INVENTION

This invention relates to apparatus and methods for inserting a foldable intraocular lens (IOL) into the eye of a patient.

BACKGROUND OF THE INVENTION

As is well known, an IOL is used to replace the natural lens of the human eye when the natural lens becomes incapable of functioning as desired. A typical IOL includes an optic or lens and one or more fixation members for fixing the IOL in the desired position within the eye.

The optic of an IOL may be constructed of hard, nondeformable materials such as polymethylmethacrylate or of soft, deformable materials such as silicone based or acrylic based materials. One advantage of the deformable IOL's is that they can be deformed into a configuration which permits them to be inserted through a smaller incision into the eye.

In deforming the IOL, the optic is typically folded in a way to cause the IOL to have smaller dimensions which enables it to be inserted through a smaller incision. An IOL which is deformed by forming it into a roll is also folded in the sense that the roll constitutes at least one fold. As used herein, a folded optic, folded IOL and folded condition have reference to an optic which is deformed in any manner, including rolling, that produces a fold.

It is desirable to compactly fold a foldable IOL because this can minimize the length of the incision necessary to insert the folded IOL into the eye. However, because IOL's are very small, they are difficult to grasp and even more difficult to fold into an efficient, compact configuration of minimal dimensions. As an example of size, the optic of a foldable IOL may be in the neighborhood of about 5 to about 7 millimeters in diameter.

Various devices have been proposed for use in inserting a foldable IOL. For example, Bartell U.S. Pat. No. 4,681,102 discloses a hingeably moveable cartridge which effectively facilitates the folding of a foldable IOL for insertion into the eye. In one useful embodiment of such an apparatus, the cartridge includes an elongated injection tube having an open distal end. The elongated injection tube receives the folded IOL from the hingeably movably portion of the cartridge. The IOL is passed out of the open distal end into the eye. Although such an insertion system is generally very effective, further enhancements, for example, in the apparent strength of the insertion system and in the ability of the system to control the release of the IOL into the eye, would be advantageous.

SUMMARY OF INVENTION

New apparatus and methods for surgically inserting a foldable IOL into an eye have been discovered. The present apparatus have sufficient strength and/or are sufficiently reinforced to insert a relatively tightly folded IOL through a small incision in the eye without breaking or bending, even though the injection portion or tube of the apparatus is made of polymeric material. In addition, the present apparatus and methods allow the IOL to be released into the eye in a uniform and controlled manner, while reducing the risk that the IOL may become mispositioned, for example, flipped, during this insertion procedure. Thus, the need for post-insertion manipulation of the IOL in the eye is advantageously reduced. Moreover, the IOL may be loaded into the present apparatus very speedily and reliably. The present apparatus are straightforward in construction and can be produced and used in a number of forms to suit the individual needs of the surgical application involved and/or the likes and dislikes of the surgeon. Practicing the present methods, the surgeon can easily and controllably place an IOL into a patient's eye through a small incision.

In one broad aspect, the present invention is directed to inserters for inserting a foldable IOL into an eye of a patient. The inserters comprise a load chamber defining a first lumen, an injection portion or tube defining a second lumen aligned with the first lumen, and a hand piece adapted to be held in the hand of a human using the inserter to insert an IOL into an eye. The load chamber is adapted to receive an IOL and to maintain the IOL in a folded state when the IOL is located in the first lumen. The injection tube has a proximal end portion, a distal end portion and an open distal end in communication with the second lumen, and is adapted to receive the folded IOL from the first lumen. The hand piece includes a bore having an opening adapted to receive the load chamber so that the proximal end portion of the injection tube is in reinforcing contact with the hand piece, preferably in abutting relation to the wall of the bore of the handpiece. The distal end portion of the injection tube extends distally of the hand piece. Using a hand piece which is in reinforcing contact with the proximal end portion of the injection tube enhances the apparent strength of the injection tube. Thus, even though the injection tube is made of a polymeric material, as is preferred, the injection tube has sufficient apparent or reinforced strength to pass a relatively tightly folded IOL through the second lumen thereof and into a small incision in the eye without the injection tube breaking, bursting, or otherwise being distorted in configuration. This adds greatly to the usefulness and reliability of the present apparatus.

The load chamber and injection tube are preferably made of polymeric material, while the hand piece is preferably made of a metal.

The second lumen, defined by the injection tube, preferably has a smaller average cross-sectional area than does the first lumen. The proximal end portion of the injection tube has a wall thickness which is greater than the wall thickness of the distal end portion. This increased wall thickness is effective to add further additional strength to the injection tube. The distal end portion of the injection tube can have a relatively thin wall thickness so that it can be inserted into the eye through a small incision, for example, an incision of about 3.2 or about 3.0 or about 2.8 mm or less. The open distal end of the injection tube is such that the folded IOL from the second lumen passes through it to be inserted into the eye.

In one embodiment, the present inserters include a push rod sized and adapted to be passed through the bore of the hand piece, the first lumen of the load chamber and at least a portion of the second lumen of the injection tube to facilitate or urge the passage of an IOL from the first lumen through the second lumen and into an eye. In a particularly useful embodiment, the hand piece and push rod include segments with mutually engageable threads so that the push rod can be threaded onto the hand piece to pass the push rod through the bore of the hand piece. This threaded embodiment is very effective in controlling the movement of the folded IOL through the first and second lumens and into the eye.

In another broad aspect of the invention, the present IOL inserters comprise a load chamber having a top, defining a first lumen and being adapted to receive an IOL and to maintain the IOL in a folded state when the IOL is located in the first lumen; and an injection tube which defines a second lumen aligned with the first lumen and is adapted to receive the folded IOL from the first lumen. The injection tube has a proximal end portion, a distal end portion and an open distal end in communication with the second lumen and through which the folded IOL from the second lumen passes to be inserted into the eye. In this aspect of the invention, the open distal end of the injection tube is beveled, preferably so that the open distal end faces generally toward the right when the top of the load chamber is positioned to be the uppermost portion of the load chamber and the inserter is viewed from above. The beveling of the distal end opening is effective to reduce the size of the incision in the eye through which the distal end portion of the injection tube can pass relative to a substantially identical (for example, in cross-sectioned area) injection tube including a distal end opening which is not beveled. The generally right facing beveled distal end opening, described herein, facilitates the passing of the IOL from the second lumen through the open distal end so that the IOL is released in the eye in a uniform and controlled manner, for example, with reduced risk of the IOL becoming mispositioned, e.g. flipped, during insertion into the eye. Using such an inserter, the IOL can be controllably and uniformly released into the eye in the desired position so that a reduced amount of manipulation of the IOL is required to properly place the IOL in the eye. As noted above, this is advantageous to avoid additional trauma to the eye caused by such post-insertion manipulation.

The beveled distal end opening can be employed alone or in combination with the previously described hand piece in reinforcing contact with the injection tube. In addition, unless expressly stated otherwise or unless two or more features are mutually inconsistent, each of the features described herein can be used in combination with any one or more of the other features described herein, and all such apparatus and methods are within the scope of the present invention.

As noted above, the open distal end of the injection tube is preferably beveled, more preferably at an angle of about 30° to about 60° and still more preferably at an angle of about 45°, relative to the longitudinal axis of the inserter. Such beveling has been found to advantageously reduce the minimum size of incision through which the distal end portion of the injection tube can be passed relative to a substantially identical injection tube including an open distal end which is not beveled.

In a particularly useful embodiment, the injection tube further comprises a through slot which extends from the open distal end of the injection tube and terminates distally of the proximal end portion of the injection tube. This through slot is effective to allow for some flexibility in the distal end portion of the injection tube so that a smaller incision in the eye may be utilized for insertion of the IOL. The length of the through slot is preferably such as to provide such advantageous degree of flexibility while, at the same time, not compromising the integrity of the injection tube so that the configuration and structural integrity of the injection tube is substantially maintained. In addition, the width of the through slot is preferably such that the fixation member or members of the IOL do not stick in or grab onto the through slot. Thus, the through slot is preferably configured so that the fixation member or members are passed through the second lumen and into the eye without grabbing onto the through slot. The through slot is preferably elongated in a direction substantially parallel to the longitudinal axis of the inserter. In a useful embodiment, with the distal end opening of the injection tube being beveled, the through slot intersects the open distal end at or near the proximal most portion of the open distal end.

The combination of a beveled open distal end, preferably a generally right facing beveled open distal end, and the through slot of the injection tube enhances the controllability of releasing the IOL into the eye. An inserter system including this combination of features has been found to reduce the risk that the IOL will become mispositioned in the inserter. Thus, the IOL is advantageously released in the eye in the desired position or orientation so that a reduced amount of post-insertion manipulation of the IOL is required.

In one embodiment of the invention, the inserter further comprises a holding element, preferably extending from the top of the load chamber, sized and adapted to be held in the hand of a human user of the inserter. This holding element is effective, for example, in placing the load chamber into the hand piece.

In a very useful embodiment, the load chamber comprises first and second members which are moveable, preferably hingeably moveable, relative to each other to place the load chamber in an opened position or in a closed position. The first and second members are preferably sized and adapted to receive an IOL in an unfolded state between the first and second members when the load chamber is in the opened position. The first and second members are sized and adapted to fold the IOL into a folded state as at least one of the first and second members are moved to place the load chamber in the closed position. In the closed position, the first and second members together define at least a portion of the first lumen of the load chamber.

Methods for inserting an IOL into a small incision in the eye, for example, using the present apparatus, are included within the scope of the present invention. In general, such methods comprise placing an IOL in an inserter as described herein; placing the open distal end of the injection tube at least partially into an eye; and causing the IOL to pass out of the open distal end of the injection tube and into the eye. In the event the load chamber includes first and second members, as described herein, the IOL is placed in the inserter so that the IOL in an unfolded state is located between the first and second members with the load chamber in the opened position. At least one of the first and second members is moved so as to place the load chamber in the closed position, thereby folding the IOL into a folded state. The open distal end of the injection tube is placed at partially into an eye and the folded IOL is caused to pass out of the open distal end of the injection tube and into the eye.

The foldable IOL's insertable in the eye using the present apparatus and methods may be of any configuration suitable to perform the desired function in the eye. Such lenses often include a lens body or optic which has optical properties in the eye. Such lens body is foldable as set forth herein. In many instances, the lens body is generally circular. However, other configurations are also useful. In addition, the IOL's may, and preferably do, include at least one flexible fixation member which is secured or attached to the optic. This flexible fixation member acts to fix the IOL in position in the eye. Examples of flexible fixation members include flexible haptics which are preferably radially resilient and extend outwardly from the periphery of the lens body. Specific examples of such flexible haptics include plate haptics and those commonly known as J-loops and C-loops. Such haptics engage appropriate circumferential eye tissue adjacent the iris or within the capsular bag to fix the lens in position in the eye. A very useful IOL includes a plurality of, especially two, such flexible haptics.

The lens body may be made of any suitable material such as acrylic polymers, silicone polymers, hydrogel-forming polymers or other well known materials for foldable IOL instruction. The present inserter systems are particularly effective with IOLs having optics including silicone polymers. Preferably, the optic also includes an ultraviolet light absorber. The flexible fixation member or members may be made of any suitable material such as polymethamethacrylate, polypropylene, nylon, silicone polymers or other materials suitable for implantation into the eye.

As used herein, the terms "foldable" and "deformable" mean that an IOL, and in particular the lens body or optic of an IOL, can be temporarily reshaped so as to pass through a smaller incision relative to the incision required if the IOL was not temporarily reshaped.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is a front side view, in perspective, of an apparatus in accordance with the present invention with the load chamber in the opened position.

FIG. 2 is a front side view, in perspective, of the apparatus shown in FIG. 1 with the load chamber in the closed position.

FIG. 3 is a front side view, in perspective, of the apparatus shown in FIG. 2 loaded into a hand piece.

FIG. 4 is a side view, partly in cross-section, taken generally along line 4—4 of FIG. 3.

FIG. 5 is a somewhat schematic illustration showing the apparatus shown in FIG. 3, with the hand piece partially in cross-section, being used to insert an IOL into an eye.

DETAILED DESCRIPTION OF THE DRAWINGS

FIG. 1 shows an IOL inserter, shown generally at 10, including a load chamber 12 and an injection tube 14. Inserter 10 is an integrally formed, for example, molded, unit made of polymeric material, such as polypropylene or the like materials. Load chamber 12 includes a first member 16 and a second member 18 which are secured or joined together and are hingeably moveable relative to each other along line 20, which is parallel to the longitudinal axis 30 of inserter 10.

Injection tube 14 includes a proximal end portion 22, a distal end portion 24 and an open distal end 26. A reinforcing collar 28 is coincidental with the proximal end portion 22 of injection tube 14.

Open distal end 26 is beveled at an angle of about 45° relative to the longitudinal axis 30 of the inserter 10.

Injection tube 14 includes a through slot 32 which extends from the open distal end 26 distally and terminates prior to the proximal end portion 22 of injection tube 14. Through slot 32 is elongated in a direction parallel to the longitudinal axis 30 of inserter 10.

As shown in FIG. 1, inserter 10 is in the opened position. In contrast, in FIG. 2, inserter 10 is shown in the closed position. In the closed position, the load chamber 12 includes a top 33 which is a combination of top surfaces 34 and 36 of first wing 38 and second wing 40, respectively, of first member 16 and second member 18, respectively. First and second wings 38 and 40 are effective for a human user of inserter 10 to hold and manipulate the inserter 10 while using it, as described hereinafter.

Inserter 10 is described in more detail with reference to FIG. 4, which shows the inserter in combination with hand piece 70. When used in combination with hand piece 70, the load chamber 12 of inserter 10 is in the closed position, as shown in FIG. 2. With the load chamber 12 in the closed position, and top 33 being the uppermost portion of the load chamber, open distal end 26 of injection tube 14 is beveled at an angle of 45° relative to the longitudinal axis 30 of the inserter 10 so that the open distal end is generally right facing (when the inserter is viewed from above). In addition, through slot 32 intersects the open distal end 26 at the proximal most portion of the open distal end, as shown in FIGS. 1, 2 and 4.

Referring to FIG. 4, with load chamber 12 in the closed position, the load chamber defines a first lumen 52 which is elongated in a direction parallel to the longitudinal axis 30 of inserter 10. Injection tube 14 defines a distally tapering second lumen 54. The average cross-sectional area of second lumen 54 transverse to the longitudinal axis 30 is smaller than or reduced relative to the average cross-sectional area of the first lumen 52. The reinforcing collar 28, which is coincidental with the proximal end portion 22 of injection tube 14, has sufficient wall thickness so that the proximal end portion of the injection tube has a larger or greater wall thickness than the distal end portion 24 of the injection tube.

The first lumen 52 is aligned with the second lumen 54 so that a folded IOL in the first lumen can be passed directly from the first lumen into the second lumen. The proximal portion 58 of the second lumen 54 is defined by the proximal end portion 22 of the injection tube 14. This proximal portion 58 of second lumen 54 has a tapering cross-sectional area transverse to the longitudinal axis 30 of the inserter 10, with the cross-sectional area decreasing in the distal direction. The taper of proximal portion 58 is more severe than the slight taper which exists in the distal portion 60 of the second lumen 54. The more severe taper in the proximal portion 58 is effective to further fold the IOL as the IOL is passed into the second lumen 54. This further folding is advantageous because the further folded IOL can be inserted into the eye through a smaller incision. The reinforcing collar 28 and the increased wall thickness of the proximal end portion 22 of injection tube 14 adds to the apparent strength of the injection tube.

With reference to FIG. 3, inserter 10 is shown in combination with hand piece 70 and push rod member 72. Hand piece 70 includes a relatively large, elongated first through opening 74 and a relatively small, elongated second through opening 76. Hand piece 70 includes a through bore 78 which extends from the proximal end 80 to the distal end 82 of the hand piece. The proximal end portion 84 of hand piece 70 includes threads 86 which are adapted to engage and mate with threads 88 of the proximal segment 90 of push rod member 72. Rod element 92 of push rod member 72 is adapted to pass through bore 78, first lumen 52, second lumen 54 and out of open distal end 26. Hand piece 70 and push rod member 72 are made of metal, such as surgical grade stainless steel or the like metals.

Inserter 10 is operated and functions as follows. When it is desired to load an IOL into inserter 10, the inserter is placed, for example, manually placed, in a configuration as shown in FIG. 1. With load chamber 12 in the opened position, an IOL, such as is shown generally at 100, is placed, for example, using forceps, in between first and second members 16 and 18. This placement is such that the anterior face 102 of optic 104 faces upwardly, as shown in FIG. 1. The filament haptics 106 and 108 of IOL 100 are located as shown in FIG. 1, so that the fixation members are located generally parallel to, rather than transverse to, the longitudinal axis 30.

With IOL 100 placed as shown in FIG. 1, first and second members 16 and 18 are hingeably moved relative to each other, for example, by manually bringing first and second wings 38 and 40 together, to place the load chamber 12 in the closed position, as shown in FIG. 2. With load chamber 12 in the closed position, IOL 100 is in a folded state, that is optic 104 is folded. The relative movement of first and second members 16 and 18 to move the load chamber from the open position to the closed position is effective to fold the lens. The folded IOL 100 is now located in the first lumen 52. For clarity sake, the folded IOL is not shown in any of FIGS. 2, 3, 4 or 5.

With the inserter 10 configured as shown in FIG. 2 and folded IOL 100 located in first lumen 52, the inserter 10 is placed in association with hand piece 70, as shown in FIG. 3. In this configuration, the distal end portion 24 of injection tube 14 extends distally beyond the distal end 82 of hand piece 70. As shown in FIG. 4, the distal portion 85 of hand piece 70 includes an inner wall 87 which is configured to receive reinforcing collar 28 in abutting relation. This abutting contact between hand piece 70 and reinforcing collar 28 adds to the apparent strength of the injection tube 14 so that folded IOL 100 can be passed from the first lumen 52 into the second lumen 54 (so that the folded IOL 100 can be further folded so as to be inserted into the eye through a smaller incision), through the second lumen and out of the open distal end 26 without breaking, bursting or otherwise distorting the configuration of the injection tube.

With inserter 10 so placed relative to hand piece 70, push rod member 72 is placed into the through bore 78 of the hand piece starting at the proximal end 80. As threads 88 come in contact with and engage threads 86, the push rod member 72 is rotated, as shown in FIG. 5, so as to thread the push rod member onto the proximal end portion 84 of hand piece 70. By gradually moving push rod element 92 through bore 78 of hand piece 70, the folded IOL 100 is urged to move from first lumen 52 into second lumen 56, through open distal end 26 and into the eye.

Referring now to FIG. 5, the IOL 100 is to be placed in eye 120 into an area formerly occupied by the natural lens of the eye. FIG. 5 shows the sclera 122 having an incision through which the distal end portion 24 of injection tube 14 is passed. Alternately, the incision can be made through the cornea. Distal end portion 24 has a sufficiently small cross-section to pass into the eye 120 through a 3.0 mm incision in the sclera 122.

The injection tube 14 is manipulated within eye 120 until it is positioned so that IOL 100 can be properly positioned in eye 120, that is in the anterior chamber, the posterior chamber, the capsular bag 124 or in the sulcus, after being released. Thus, the surgeon is able to controllably position the distal end portion 24 of injection tube 14, with IOL 100 in the first lumen 52 of load chamber 12. Once distal end portion 24 is so positioned, the rod element 92 is urged distally, by rotating (threading) push rod member 72 onto hand piece 70, to pass the IOL 100 into and through the second lumen 54, through the open distal end 26 of injection tube 14 and into the eye 120. The anterior face 102 of IOL 100 faces generally forwardly in the eye 120 as the IOL is released from the inserter 10. In other words, the IOL 100 passes through first lumen 52, second lumen 54 and open distal end 26 and into eye 120 without flipping or otherwise becoming mispositioned. Only a relatively small amount of, if any, post-insertion re-positioning is needed to properly position IOL 100 in eye 120.

After the IOL 100 has been inserted into the eye 120, the rod element 92 is moved proximally into the injection tube 14 and the distal end portion 24 of the injection tube is removed from the eye 120. If needed, the IOL 100 can be re-positioned in the eye 120 by a small, bent needle or similar tool inserted into the same incision. The use of the present insertion apparatus reduces or minimizes the need for post-insertion manipulation of IOL 100.

Once the IOL 100 is properly positioned in eye 120 and inserter 10 is withdrawn from the eye, the incision in the sclera 122 may be mended, for example, using conventional techniques. After use, inserter 10 is preferably disposed of. Hand piece 70 and push rod member 72 can be reused, after sterilization/disinfection.

The present IOL insertion apparatus and methods are straightforward and easy to use and practice. The present invention provides for an effective and controlled insertion of foldable IOLs into eyes. The present system very conveniently provides for precise positioning of the IOL in the eye and controlled IOL release so as to reduce, or even eliminate, the risk of damaging the eye as a result of IOL insertion or post surgical manipulation to properly position the IOL in the eye.

While this invention has been described with respect of various specific examples and embodiments, it is to be understood that the invention is not limited thereto and that it can be variously practiced within the scope of the following claims.

What is claimed is:

1. An inserter for inserting a foldable intraocular lens into an eye of a patient comprising:

a load chamber having a top having an uppermost position and joined to said top, at least one member defining a first lumen, said load chamber being adapted to receive an intraocular lens in a folded state when the intraocular lens is located in said first lumen, said top extending radially further from said first lumen than said at least one member; and an injection tube joined to said load chamber, defining a second lumen aligned with said first lumen, and being adapted to receive the folded intraocular lens from the first lumen, said injection tube having a proximal end portion, a distal end portion and an open distal end in communication with said second lumen and through which the folded intraocular lens from said second lumen passes to be inserted into an eye, said open distal end being beveled so that said open distal end faces toward the right when said top is at its uppermost position and said inserter is viewed from directly above the top with said distal end portion extending distally away.

2. The inserter of claim 1 which further comprises a hand piece adapted to be held in the hand of a human using said inserter to insert an intraocular lens into an eye, said hand piece including a bore having an open distal end adapted to receive said load chamber so that said proximal end portion of said injection tube is in reinforcing contact with said hand piece and said distal end portion of said injection tube extends distally from said open distal end of said hand piece.

3. The inserter of claim 2 wherein said proximal end portion of said injection tube is in abutting relation to said hand piece.

4. The inserter of claim 2 which further comprises a push rod sized and adapted to be passed through said bore, said first lumen and at least a portion of said second lumen to facilitate the passage of an intraocular lens from said first lumen through said second lumen and into an eye.

5. The inserter of claim 1 wherein said inserter has a longitudinal axis and said open distal end is beveled at an angle in the range of about 30° to about 60° relative to the longitudinal axis of said inserter.

6. The inserter of claim 1 wherein said injection tube further comprises a through slot which extends to said open distal end and terminates distally of said proximal end portion.

7. The inserter of claim 6 wherein said open distal end has a proximal most portion and said through slot intersects said open distal end at or near the proximal most portion of said open distal end.

8. The inserter of claim 1 wherein said load chamber comprises first and second members which are moveable relative to each other to place said load chamber in an opened position or in a closed position, and said first and second members are sized and adapted to receive an intraocular lens in an unfolded state between said first and second members when said load chamber is in the opened position and to fold the intraocular lens into a folded state as at least one of said first and second members are moved to place said load chamber in the closed position.

9. The inserter of claim 8 wherein said first and second members are hingeably moveable relative to each other.

10. The inserter of claim 9 wherein said first and second members define said first lumen with said load chamber in the closed position.

11. The inserter of claim 8 wherein said first and second members define said first lumen with said load chamber in the closed position.

12. The inserter of claim 11 wherein first and second wings are joined to and extend away from said first and second members, respectively, and define said top of said load chamber with said load chamber in the closed position.

13. The inserter of claim 1 which further comprises a hand piece adapted to be held in the hand of a human using said inserter, said hand piece including an open distal end and a bore having a laterally extending opening through which said load chamber is received in said bore, said top of said load chamber extends outwardly from said laterally extending opening and said distal end portion of said injection tube extends distally from said open distal end of said hand piece when said load chamber is received in said bore.

14. The inserter of claim 1 wherein said load chamber has a closed position and a wing is joined to and extends away from said at least one member and defines said top of said load chamber with said load chamber in the closed position.

15. A method for inserting an intraocular lens into a small incision in an eye, comprising:

placing an intraocular lens in the inserter as defined in claim 8 so that said intraocular lens in an unfolded state is located between said first and second members with said load chamber in the opened position;

moving at least one of said first and second members so as to place said load chamber in the closed position, thereby folding said intraocular lens into a folded state;

placing said distal end of said injection tube at least partially into an eye; and causing said intraocular lens to pass out of said open distal end of said injection tube and into the eye.

16. A method for inserting an intraocular lens into a small incision in an eye, comprising:

placing an intraocular lens in the inserter as defined in claim 1;

placing said open distal end of said injection tube at least partially into an eye; and causing said intraocular lens to pass out of said open distal end of said injection tube and into the eye.

* * * * *